United States Patent
van Haveren et al.

(10) Patent No.: US 9,376,414 B2
(45) Date of Patent: Jun. 28, 2016

(54) PROCESS AND INTERMEDIATES FOR THE PRODUCTION OF FURAN-2,5-DICARBOXYLIC ACID OR DERIVATIVES THEREOF

(71) Applicant: Stichting Dienst Landbouwkundig Onderzoek, Wageningen (NL)

(72) Inventors: Jacobus van Haveren, Wageningen (NL); Daniël Stephan van Es, Wageningen (NL); Frits van der Klis, Wageningen (NL); Henricus Wilhelmus Carolina Raaijmakers, Wageningen (NL)

(73) Assignee: Stichting Dienst Landbouwkundig Onderzoek, Wageningen (NL)

( * ) Notice: Subject to any disclaimer, the term of this patent is extended or adjusted under 35 U.S.C. 154(b) by 0 days.

(21) Appl. No.: 14/786,723

(22) PCT Filed: May 8, 2014

(86) PCT No.: PCT/NL2014/050293
§ 371 (c)(1),
(2) Date: Oct. 23, 2015

(87) PCT Pub. No.: WO2014/182171
PCT Pub. Date: Nov. 13, 2014

(65) Prior Publication Data
US 2016/0075672 A1 Mar. 17, 2016

(30) Foreign Application Priority Data
May 8, 2013 (EP) .................................... 13167035

(51) Int. Cl.
*C07D 307/68* (2006.01)
*C07D 307/46* (2006.01)
*C07D 307/56* (2006.01)

(52) U.S. Cl.
CPC ............ *C07D 307/68* (2013.01); *C07D 307/56* (2013.01)

(58) Field of Classification Search
USPC ................................................ 549/485, 484
See application file for complete search history.

(56) References Cited

U.S. PATENT DOCUMENTS 9,260,403 B2 * 2/2016 Yoshikuni ............ C07D 307/68

FOREIGN PATENT DOCUMENTS

WO 2013049711 4/2013

OTHER PUBLICATIONS

Berndt, H. et al., "Oxygen adsorption on Au/Al2O3 catalysts and relation to the catalytic oxidation of ethylene glycol to glycolic acid," Applied Catalysis A: General, 244 (2003), 169-179.
Feather, M.S. et al., "Relationships between Some Uronic Acids and Their Decarboxylation Products," Journal of Organic Chemistry, ACS, US, vol. 31, No. 12, 1966, pp. 4018-4021.
Moldenhauer, "Justus Liebigs Annalen der Chemie," 1953, 580, 169-187.
Prati, L., et al., "New Gold Catalysts for Liquid Phase Oxidation," Gold Bulletin, 32(3) (1999), 96-101.
Stutz, E. et al., Helvetica Chimica Acta Volumen XXXIX, Fasciculus VII (1956), No. 245, 2126-2130.
Taarning, E., et al., "Chemicals from Renewables: Aerobic Oxidation of Furfural and Hydroxymethylfurfural over Gold Catalysts," ChemSusChem, (2008), 1, 75-78.
Van Putten, R., et al., "Hydroxymethylfurfural, A Versatile Platform Chemical Made from Renewable Resources," Chem. Rev. (2013), 113, 1499-1597.
Wolf, A., et al., "A systematic study of the synthesis conditions for the preparation of highly active gold catalysts," Applied Catalysis A: General 226 (2002), 1-13.

* cited by examiner

*Primary Examiner* — Charanjit Aulakh
(74) *Attorney, Agent, or Firm* — Patterson Intellectual Property Law, P.C.; James R. Cartiglia; Timothy L. Capria

(57) ABSTRACT

Disclosed is a method of making 5-formyl-2-furoic acid and furan-2,5-dicarboxylic acid. The method involves the use of 5-keto-aldonic acids as intermediates, as these can be subjected to ring formation by a cyclodehydration reaction under mild conditions. The 5-formyl-2-furoic acid or carboxylic derivative thereof is subjected to oxidation so as to form furan-2,5-dicarboxylic acid. The 5-keto-aldonic acid intermediates can be obtained by isomerization of uronic acids which can be obtained from sugar beet pulp, chicory pulp, fruit peals including orange peels, or non-terrestrial sources like seaweeds. A preferred source is sugar beet pulp.

15 Claims, No Drawings

PROCESS AND INTERMEDIATES FOR THE PRODUCTION OF FURAN-2,5-DICARBOXYLIC ACID OR DERIVATIVES THEREOF

FIELD OF THE INVENTION

The invention pertains to the synthesis of furan-2,5-dicarboxylic acid (FDCA) or carboxylic derivatives thereof. Particularly, the invention pertains to a route to FDCA, and to 5-formyl-2-furoic acid (FFA) as an intermediate therein, from bio-based uronic acids. Such uronic acids can be obtained from sources, like sugar beet pulp, chicory pulp, fruit peals including orange peels, or non-terrestrial sources like seaweeds. Alternatively, such uronic acids can be obtained by the oxidation of the primary hydroxyl group of the corresponding aldoses.

BACKGROUND OF THE INVENTION

The invention relates to unlocking the potential of renewable biomass, for the production of economically valuable functional chemicals. One such chemical is furan-2,5-dicarboxylic acid (FDCA). FDCA is useful, inter alia, as a building block for polymers. In fact, it potentially serves as an alternative for terephthalic acid in the production of polyesters. FDCA based polyesters, including PEF, poly(ethylene furanoate), have been shown to be highly comparable to their terephthalate based analogues.

Although historically FDCA was first synthesized from galactaric acid, the far majority of current research efforts focuses on the use of hexoses (i.e. D-glucose and D-fructose) as starting materials and 5-hydroxymethyl-2-furaldehyde (HMF) as an intermediate (Scheme 1).

Over the past decades, many routes towards HMF have been explored, the far majority of these studies relating to glucose and fructose as starting components. Besides the routes depicted in scheme one, literature mentions failed attempts to obtain more than minute amounts of HMF by acid catalyzed dehydration of uronic acids like galacturonic or glucuronic acid.

A single publication (Votocek 1934) mentions the dehydration of a keto acid derived from sorbose, viz. by oxidation of sorbose (neutral sugar) into 5-ketogluconic acid. The highest yields of HMF are generally obtained starting from D-fructose, which is generally produced from starch containing food crops, but can also be obtained from sources like sucrose or inulin. Therefore, whereas this first generation HMF may contribute to the reduction of greenhouse gas emissions and non-renewable energy consumption, there is a potential conflict with food production.

Hence it would be desirable to develop a route to FDCA based on the use of non-food lignocellulosic feed-stocks like wood or grasses, or even more preferably from residues from agro-food production or from non-terrestrial biomass sources, in which case there is no competition with current land use.

One such abundantly available type of residues are pectins; (hetero)polysaccharides which are found in large amounts in sugar beet and chicory pulp and fruit peals. Pectins can be hydrolyzed into the free sugar monomers like galacturonic acid, arabinose, glucose, galactose, rhamnose, xylose, and efforts are being undertaken to scale up the process to an economically viable industrial scale. In this way, a significant stream of non-edible uronic acids, i.e. D-galacturonic acid, or D-glucuronic acid becomes available, which can serve as a starting material for non-food applications, such as synthetic

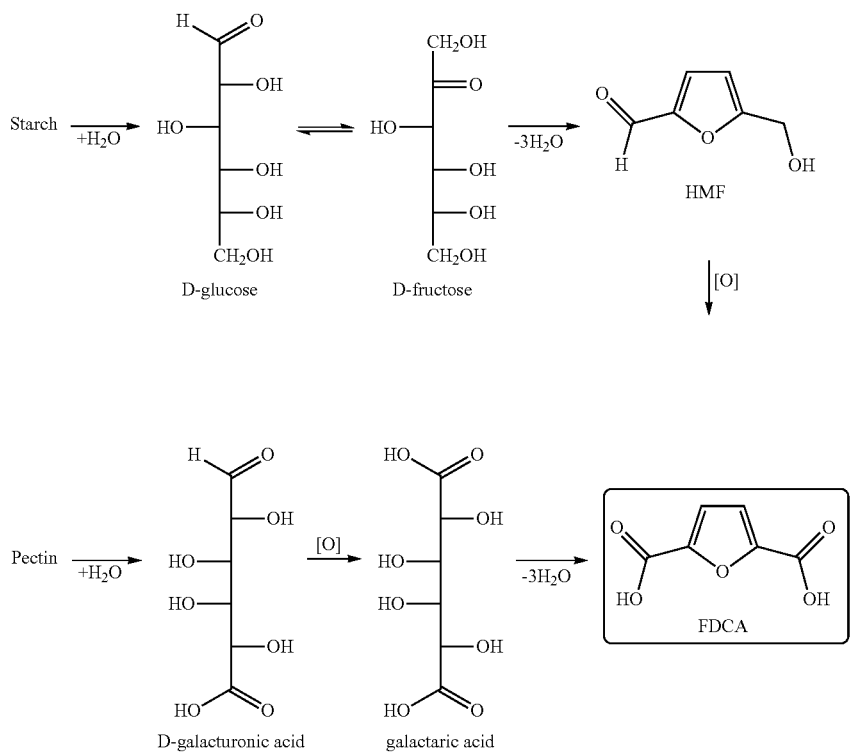

polymers. Seaweeds, like brown seaweeds of numerous types, can also serve as a source in order to obtain uronic acids like D-mannuronic acid and L-guluronic acid, by hydrolysis of the alginate fraction of seaweeds.

A method for preparing FDCA from renewable sources such as alginate is described in WO 2013/049711. Herein 5-formyl-2-furan dicarboxylic acid (FFA) is oxidized to produce FDCA. The FFA is obtained from a specific intermediate that satisfies the following formula:

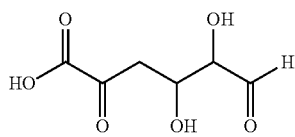 [SMILES: O=CC(O)C(O)CC(=O)C(=O)O]

This compound is either 4-deoxy-L-erythro-5-hexoseulose (or hexosulose) urinate (DEHU) or 4-deoxy-L-threo-5-hexosulose urinate (DTHU). Accordingly, for practicing the method disclosed in WO 2013/049711, it is required that the renewable source, viz. the alginate, is subjected to a specific enzymatic cleavage method resulting in DEHU or DTHU. Therewith the method does not provide a straightforward way of valorizing the biomass concerned. Also, from a chemical point of view the intermediate, particularly by having a keto group adjacent to a carboxylic acid group, runs a risk of being unstable.

It is now desired to provide a method for the production of FDCA that commences with starting materials that, if desired, are abundantly available from bio-based sources, viz. the aforementioned uronic acids.

A problem with uronic acids, such as galacturonic acid, is that they are not stable under strong acidic conditions, as these lead to decarboxylation reactions. As a background in this respect, reference is made to Stutz et al., Helvetica Chimica Acta Volumen XXXIX, Fasciculus VII (1956), No. 245, 2126-2130. Therein it is mentioned that several degradation products result when hexuronic acids are treated with concentrated sulfuric acid. In the paper, FFA is resolved as being one of the degradation products resulting from treating D-galacturonic acid with concentrated sulfuric acid. The yield of FFA hereby is very low, viz. 25 mg FFA on the basis of 10 g galacturonic acid.

In a co-pending patent application [unpublished EP application number 12163081], we have shown that uronic acids, particularly galacturonic acid can serve as starting material for the synthesis of FDCA if conducted according to the above Scheme 1. In the first step, galacturonic acid is converted to galactaric acid (also known as mucic acid) by using a mild catalytic oxidation. This reaction proceeds fast and very selectively in aqueous media at room temperature, requiring only air as the oxidant. The subsequent cyclodehydration step however is prone to have only moderate yields (<50 mole %). In order to become economically viable, this second step needs to be significantly improved.

Therefore, an alternative synthesis strategy is desired to be able to obtain FDCA from uronic acids.

SUMMARY OF THE INVENTION

In order to address one or more of the foregoing desires, the invention, in one aspect, provides a process for the production of furan-2,5-dicarboxylic acid, or a carboxylic derivative thereof, comprising making 5-formyl-2-furoic acid, or a carboxylic derivative thereof, by a method comprising the steps of (i) providing an uronic acid; (ii) subjecting the uronic acid to isomerization so as to form the corresponding 5-keto-aldonic acid; (iii) subjecting said 5-keto-aldonic acid to cyclodehydration so as to produce 5-formyl-2-furoic acid or a carboxylic derivative thereof, and subjecting the 5-formyl-2-furoic acid, or the carboxylic derivative thereof, to oxidation so as to form furan-2,5-dicarboxylic acid, or a carboxylic derivative thereof.

In another aspect, the invention provides a method of making 5-formyl-2-furoic acid, or a carboxylic derivative thereof, the method comprising the steps of (i) providing an uronic acid; (ii) subjecting the uronic acid to isomerization so as to form the corresponding 5-keto-aldonic acid; (iii) subjecting said 5-keto-aldonic acid to cyclodehydration so as to produce 5-formyl-2-furoic acid or a carboxylic derivative thereof, wherein the uronic acid is obtained from bio-based pectins or biobased alginates.

In a still further aspect, the invention pertains to the use of a 5-keto-aldonic acid as an intermediate in the synthesis of 5-formyl-2-furoic acid or a carboxylic derivative thereof.

In yet another aspect, the invention pertains to the use of a 5-keto-aldonic acid as an intermediate in the synthesis of furan-2,5-dicarboxylic acid or a carboxylic derivative thereof.

In a final aspect, the invention pertains to an overall, bio-based process for the synthesis of furan-2,5-dicarboxylic acid, or a carboxylic derivative thereof, the process comprising the steps of (i) providing at least one bio-based uronic acid; (ii) subjecting the at least one uronic acid to isomerization so as to form the corresponding 5-keto aldonic acid; (iii) subjecting said 5-keto-aldonic acid to cyclodehydration so as to produce 5-formyl-2-furoic acid or a carboxylic derivative thereof, subjecting the 5-formyl-2-furoic acid, or the carboxylic derivative thereof, to oxidation so as to form furan-2,5-dicarboxylic acid, or a carboxylic derivative thereof.

DETAILED DESCRIPTION OF THE INVENTION

In a broad sense, the invention is based on the judicious insight to direct a uronic acid, such as galacturonic acid, into a furanose configuration prior to further chemical conversion. This insight, which is based on the present inventors' finding that 5-keto-galactonic acid adopts a furanose form, has led to the recognition of 5-keto-aldonic acids as key intermediates in the synthesis of 5-formyl-2-furoic acid (FFA) and furan-2,5-dicarboxylic acid. In the context of the invention, the 5-keto-aldonic acid can be in the form of the free acid, an ester, a lactone, or a salt.

Using this intermediate, allows to avoid the presence of uronic acids, such as galacturonic acid and glucuronic acid, at a point in time where strong acidic conditions are applied. This is highly beneficial, in view of the above-mentioned problem that uronic acids, such as galacturonic acid, are not stable under strong acidic conditions, leading to decarboxylation reactions. The inventors judiciously avoided this problem by converting uronic acids into an intermediate that is more stable towards decarboxylation, but which at the same time has a higher reactivity for the desired reaction, i.e. cyclodehydration.

The synthesis route to FFA, as exemplified on the basis of D-galacturonic acid, is illustrated in Scheme 2 below.

Scheme 2

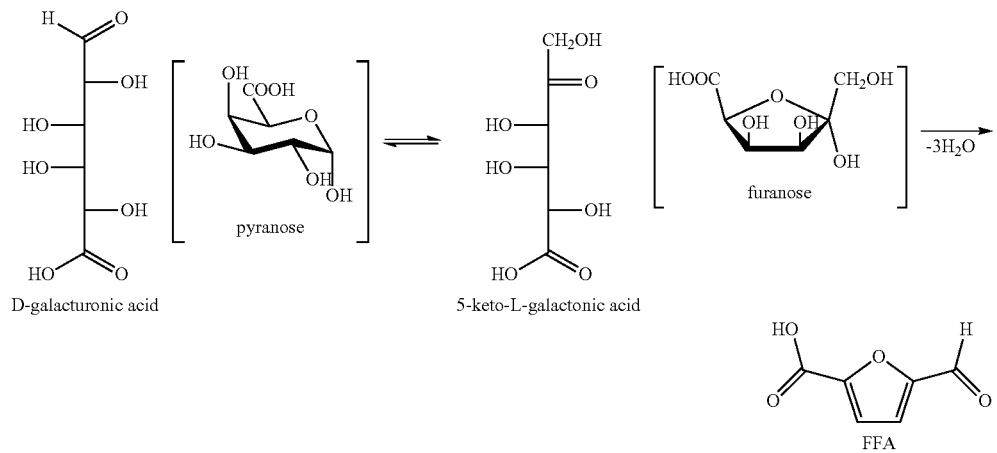

As is illustrated in the scheme, the process of the invention first provides a furanose structure, and then brings about cyclodehydration. The inventors believe that the ring closure reaction, so as to form the required furan structure, can occur under much milder circumstances if the substrate is in a furanose form compared to the pyranose or open form.

This furanose ring form is not only advantageous with regard to the furan formation, but also has the additional benefit that the furan intermediate formed (FFA) is more stable, and less susceptible to byproduct formation, than 5-hydroxymethyl furfural.

In a first aspect, the invention is directed to a method of making 5-formyl-2-furoic acid, or a carboxylic derivative thereof from bio-based pectins or bio-based alginates. The method comprises the steps of (i) providing an uronic acid obtained from said pectins or alginates; (ii) subjecting the uronic acid to isomerization so as to form the corresponding 5-keto-aldonic acid; (iii) subjecting said 5-keto-aldonic acid to cyclodehydration so as to produce 5-formyl-2-furoic acid or a carboxylic derivative thereof.

The aforementioned carboxylic derivative can be an ester or amide derivative for the carboxylic acid groups, or acetal, hemiacetal or imine for the aldehyde functionality. These derivatives will generally have up to 20 carbon atoms, preferably 1 to 12 carbon atoms, more preferably 1 to 6 carbon atoms, and most preferably 1 to 4 carbon atoms.

In another respect, the invention pertains to an intermediate that precedes the furoic acid or furoate, viz. a 5-keto-aldonic acid. The intermediate 5-keto-aldonic acids are obtainable from the desired bio-based, pectins-containing or seaweed, resources. Particularly, the intermediate can be produced by subjecting the uronic acid, e.g. D-galacturonic acid or D-glucuronic acid, to isomerization so as to form the corresponding aldonic acid, such as 5-keto-L-galactonic acid or 5-keto-mannonic acid. This isomerization is preferably conducted in alkaline water, i.e. a pH of 7 or higher, in the presence of a calcium salt, such as calcium carbonate, CaO, or $Ca(OH)_2$, as this leads to the selective precipitation of 5-keto-L-galactonic acid (mono-basic Ca-salt) at room temperature. It is also conceivable to use $NaOH/CaCl_2$. Other methods to bring about this isomerization are base catalyzed chemical isomerization, or conversions by enzymes.

Some uronic and their corresponding keto-aldonic acids are shown in Scheme 3 below.

Scheme 3

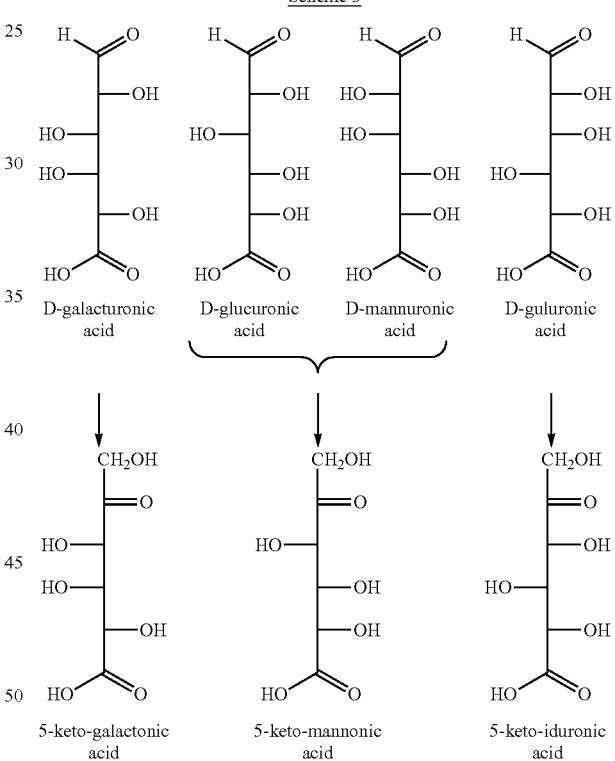

Preferably, thereby the uronic acid (or a mixture of uronic acids) such as D-galacturonic acid is retrieved by hydrolysis from a bio-based source of pectins, preferably sugar beet pulp, chicory pulp, or fruit peals. The D-galacturonic acid can be readily obtained by hydrolysis of said pectins. This hydrolysis can be conducted using methods known in the art. D-glucuronic acid can e.g. be obtained by TEMPO mediated oxidation of glucose, the glucose resulting from the hydrolysis of glucose containing polysaccharides. D-guluronic and D-mannuronic acid can be obtained by the hydrolysis of alginates, e.g. present in aquatic biomass such as brown algae The aforementioned isomerization of uronic acids so as to form the corresponding 5-keto-aldonic acids, is pivotal in the bio-based synthesis of FFA and FDCA in accordance with the invention. In this respect, the invention also pertains to the use of a 5-keto-aldonic acid as an intermediate in the synthesis of 5-formyl-2-furoic acid or a carboxylic derivative thereof, as well as in the synthesis of furan-2,5-dicarboxylic acid or a carboxylic derivative thereof.

By virtue of the route via 5-keto-aldonic acid to FFA, the invention provides an advantageous combination of a synthesis that goes via an intermediate that can be obtained via a bio-based starting material, and that also meets with a surprising ease of further processing.

The intermediate is subjected to cyclodehydration so as to produce 5-formyl-2-furoic acid, or a carboxylic derivative thereof. This reaction can be conducted, conveniently, under mild conditions in a suitable solvent, e.g. methanol, ethanol, water, or biphasic systems like water/MIKB (methyl isobutyl ketone), in the presence of an acid catalyst.

Homogeneous acids like e.g. HCl, sulfuric acid, formic acid, acetic acid, oxalic acid, hydrobromic acid, phosphorous acid or p-toluene sulfonic acid can be used as the acidic catalyst to affect the dehydration. Alternatively also Lewis acid type catalysts like $ZnCl_2$, $CuCl_2$, $BF_3$—$OEt_2$, or lanthanide salts can be used as acidic catalysts. Alternatively, the dehydration can also be conducted in the presence of heterogeneous catalysts. Suitable heterogeneous catalysts are acidic ion-exchange resins (e.g. Amberlyst or Dowex type), acidic zeolites (e.g. H-BEA zeolite), niobium phosphate based catalysts, titanium based catalyst, or zirconium phosphate, In general the dehydration can be effected with similar catalysts systems as in the dehydration of glucose and fructose to HMF. See, e.g., a review by van Putten et al., *Chem. Rev.* (2013), 113, 1499-1597.

If the solvent is an alcohol, the resulting product will be esterified by the alkyl residue of the alcohol. Hence, in the case of methanol, the product formed is methyl-5-formyl-2-furoate. The product can also be obtained either as the free aldehyde, or as the acetal or hemiacetal of the corresponding alcohol used as a solvent. The dehydration can be effected in a single phase solvent, including water, polar organic solvent like alcohols, ketones, DMSO, DMF or NMP and ionic liquids. Additionally the dehydration can also be effected in biphasic solvent systems like water/MIBK, water/DMSO, MIBK/2-BuOH. In general the dehydration can be effected in similar solvent systems as the dehydration of glucose and fructose to HMF, see the aforementioned review by van Putten et al.

The oxidation of FFA itself, can be conducted in a known manner. Reference is made, e.g., to WO 2013/049711. Another reference is Moldenhauer, Justus Liebigs Annalen der Chemie, 1953, 580, 169-187, wherein the oxidation is conducted using with $H_2O_2$ under the influence of NaOH. Another example of a suitable method involves an Au/$TiO_2$ catalyst and compressed air as the oxidant, in methanol. This method has been described as part of a pathway to oxidize 5-hydroxymethyl-2-furaldehyde (HMF) to FDCA by E. Taarning et al., *ChemSusChem*, (2008), 1, 75-78, and can be applied here in an analogous manner. Also other supported gold catalysts can be used. Such catalysts comprise support of a metal oxide, e.g. $TiO_2$ or $Al_2O_3$, or other materials customary in the art of providing supported catalysts for heterogeneous catalysis. In general, the oxidation can be conducted by subjecting the 5-formyl-2-furoic acid or carboxylic derivative thereof to molecular oxygen under the influence of a supported noble metal catalyst. The metal is preferably selected from the group consisting of gold, platinum, ruthenium and palladium. This oxidation is preferably conducted in the presence of a base.

The metal oxide support generally is a catalyst support made of at least one oxide of a main group or transition metal or metalloid, including compounds which comprise more than one metal and/or metalloid. Preference is given in this connection to oxides of metals or metalloids of main group 2 of the Periodic Table, such as MgO, CaO or BaO, oxides of metals or metalloids of main group 3 of the Periodic Table, such as $Al_2O_3$ or lanthanoid oxides or oxides of metals or metalloids of main group 4 (IVA or IVB) of the Periodic Table, such as $TiO_2$, $ZrO_2$, $SnO_2$, or $SiO_2$. Also $Fe_2O_3$ can be employed. The compounds having more than one metal and/or metalloid are preferably silicates, especially aluminosilicates. The gold comprises metallic gold, dispersed onto the support, preferably as nanoparticles.

As an alternative for the metal oxide supports, the gold can be supported on carbon supports, e.g. activated carbons, carbon blacks, graphites, carbon nanotubes, carbon nanofibers, etc. Carbon supports are preferred in the event that the oxidation is conducted in the presence of a base.

The catalyst will generally comprise, in weight percentages relative to the support, of from 0.1% to 5% of the noble metal. Preferred percentages are 0.1% to 1.5%. The metal oxide-supported noble metal catalyst is preferably employed in the form of a powder or granules.

In one embodiment, gold nanoparticles are used which generally have a diameter of below 10 nm, preferably of below 6 nm and most preferably of from 1 to 2 nm. The metal oxide-supported gold catalysts used according to the invention can be prepared, i.e. gold can be deposited in the form of nanoparticles on the metal oxide support materials, for example by employing precipitation methods where the gold is deposited in the form of oxiclic/hydroxic gold precursors by precipitation on the metal oxide support, or is precipitated together with a precursor of the metal oxide support. Au can also be introduced in the sol-gel synthesis of the support, for example of an earth metal oxide or a transition metal oxide. Also known are impregnation with gold solutions and the application of Au colloids to supports using various polymers as colloid stabilizers. Suitable methods for preparing metal oxide-supported gold catalysts include for example precipitation methods, deposition-precipitation methods and methods for chemical deposition from the gas phase (CVD methods) and are described inter alia in Prati and Martra, Gold Bulletin, 32(3) (1999), 96-101; Wolf and Schuth, Applied Catalysis A: General., 226 (2002), 1-13, and Berndt et al., Applied Catalysis A: General, 6442 (2003), 1-11.

The 5-formyl-2-furoic acid or a carboxylic derivative thereof is subjected to oxygen in order to affect the oxidation. The oxygen can be provided in an oxygen-containing gasstream. Such gas streams generally comprise at least 40% oxygen, more typically at least 60% oxygen, and may, e.g., have a purity of from 90%-100%. An advantage of the invention, is that it also works well with compressed air. Accordingly, the oxidation can be conducted under relatively mild circumstances, with a relatively cheap, and particularly abundantly available natural source of oxygen, viz. air. Alternatively, the oxidation can be conducted using hydrogen peroxide.

The oxidation can be conducted under a wide range of conditions, at, e.g., temperatures as high as 130° C. Advantageously, however, the invention allows relatively mild oxidation conditions. Accordingly, preferred temperatures range from 0° C. to 50° C., preferably from 15° C. to 35° C., and most preferably at room temperature. The low temperature is an unexpected advantage as compared to other oxidations using supported gold catalysts.

The oxidation is conducted for a suitable period of time, generally more than 0.5 hours and less than 24 hours, e.g. 1-5 hours, typically 2-3 hours.

The pH during the oxidation is generally 7-12, preferably 9-11. If the reaction is conducted in water a base is preferably present, in generally 0.5 to 5 eq., preferably 1 eq. to 1.5 eq. The oxidation can also advantageously be conducted in other media, particularly alcoholic media such as methanol. If in that case a base is employed, this can advantageously be at a lower amount, e.g. 0.05 to 0.5 eq., typically around 0.1 eq.

The method of the invention is generally conducted at atmospheric pressure, although other pressures (range 1-10 bar) can also be employed.

The invention also pertains to the overall bio-based synthesis of FDCA. This is realized by a process comprising the steps of (i) providing at least one bio-based uronic acid; (ii) subjecting the at least one uronic acid to isomerization so as to form the corresponding 5-keto-aldonic acid; (iii) subjecting said 5-keto-aldonic acid to cyclodehydration so as to produce 5-formyl-2-furoic acid or a carboxylic derivative thereof, subjecting the 5-formyl-2-furoic acid, or the carboxylic derivative thereof, to oxidation so as to form furan-2,5-dicarboxylic acid, or a carboxylic derivative thereof. This process is preferably conducted in accordance with any one of the embodiments of the invention as described above in connection with the production of FFA and of FDCA.

The invention will be illustrated hereinafter with reference to the following non-limiting examples. Percentages are indicated by weight.

Example 1

Preparation of 5-keto-L-galactonic acid (mono-basic calcium salt) from D-galacturonic acid using aqueous calcium hydroxide Calcium oxide (11.18 g, 0.199 mol) was suspended in demineralized water (10 L) and stirred for 10 min. in an open beaker. A small amount of un-dissolved particles was removed by filtration, yielding a colorless clear solution. Next, D-galacturonic acid monohydrate (40.01 g, 0.198 mol) was added under stirring to give a clear, slightly yellow, solution. After standing at room temperature for 3 days, crystals appeared which were collected by suction filtration. The initially transparent crystals were dried to a constant weight under vacuum at 40° C., over sicapent. The resulting 5-keto-L-galactonic acid (mono-basic calcium salt) was obtained as a bright yellow crystalline material (22.9 g, yield 46 mol %). and analyzed by $^1$H/$^{13}$C-NMR and IR.

Example 2

Preparation of 5-keto-L-galactonic acid (mono-basic calcium salt) from D-galacturonic acid using aqueous calcium chloride and sodium hydroxide Calcium chloride (2.62 g, 23.57 mmol) and D-galacturonic acid monohydrate (5 g, 23.57 mmol) were dissolved in 100 mL demineralized water to give a clear yellow solution (acidic pH). A concentrated solution of sodium hydroxide (1.89 g, 47.14 mmol) in demineralized water (10 mL) was added drop wise over a period of 5 min. After addition was complete, the resulting slightly turbid solution (alkaline pH) was placed in the refrigerator (7° C.) for 3 days. The formed crystals were collected by suction filtration. The initially transparent crystals were dried to a constant weight under vacuum at 40° C., over sicapent. The resulting 5-keto-L-galactonic acid (mono-basic calcium salt) was obtained as a bright yellow crystalline material (4.12 g, yield 70 mol %) and analyzed by $^1$H/$^{13}$C-NMR and IR.

Example 3

Preparation of 5-keto-L-galactonic acid (mixture of the free acid and lactones) from 5-keto-L-galactonic acid (mono-basic calcium salt)

5-keto-L-galactonic acid (mono-basic calcium salt) (0.5 g, 2 mmol) was suspended in 50 mL demineralized water. Amberlite IR-120 resin (H$^+$ form, 3 g) was added to the yellow suspension and the resulting mixture was placed in an ultrasonication bath for 10 min. Subsequently, the resin was separated by filtration and washed with 10 mL demineralized water. The combined clear aqueous solution was concentrated using a rotary evaporator at 60° C., and the resulting yellowish oil was further dried in a vacuum oven, 40° C., 50 mbar, over Sicapent for 19 h. The resulting 5-keto-L-galactonic acid (mixture of the free acid and lactones, 0.410 g, 106% yield) was obtained as a dark yellow gum, still containing a small amount of water.

Example 4-6

Preparation of methyl 5-formyl-2-furoate (mixture of free aldehyde and dimethyl acetal) from 5-keto-L-galactonic acid (mono basic calcium salt)

General Procedure:
50 mL round bottom flasks were equipped with magnetic stirring bars, reflux condensers with N$_2$-inlet and 5-keto-L-galactonic acid mono-basic calcium salt (1.0 g, 4 mmol). Methanolic HCl (3 M solution, 10 mL) was charged, upon which the yellow crystals dissolved immediately to give a clear colorless solution. The reaction mixtures were subsequently heated to reflux (65° C.) for the desired period of time. The resulting clear red-brown solutions were allowed to cool down to room temperature and 10 mL of demineralized water was added. After 45 min. the aqueous mixtures were extracted with diethyl ether (3×20 mL). The combined organic layers were then washed with brine until the pH of the water layer was neutral. The organic layers were dried over MgSO$_4$, filtered and concentrated at 40° C. under vacuum using a rotary evaporator. The resulting products were obtained as red-brown oils which crystallized within a few minutes after cooling to room temperature. The products were analyzed by GC-MS and NMR.

The product mixtures consisted of methyl 5-formyl-2-furoate (free aldehyde) and methyl 5-formyl-2-furoate (dimethyl acetal) which were easily separated by column chromatography (silicagel, petroleum ether/ethyl acetate 75:25) to give the pure compounds as slightly yellow crystalline solids. The products were analyzed by GC-MS and NMR. The results are shown in Table 1.

TABLE 1

Results of the preparation of methyl 5-formyl-2-furoate (free aldehyde and dimethyl acetal) from 5-keto-L-galactonic acid (mono basic calcium salt). Conditions: 5-keto-L-galactonic acid (mono basic calcium salt), (1.0 g, 4 mmol), methanolic HCl (3M solution, 10 mL).

| Example | Temp (° C.) | Time (h) | Crude product yield (mol %)[a] |
|---------|-------------|----------|-------------------------------|
| 4 | 65 | 24 | 65 |
| 5 | 65 | 48 | 54 |
| 6 | 65 | 72 | 50 |

[a]Mixture of methyl 5-formyl-2-furoate and methyl 5-formyl-2-furoate dimethyl acetal.

Analytical Data:

Methyl 5-formyl-2-furoate (free aldehyde)

$^1$H NMR (400.17 MHz, CDCl$_3$): δ=9.82 (1H, s), 7.29-7.26 (2H, m), 3.96 (3H, s).
$^1$H NMR (400.17 MHz, DMSO-D$_6$): δ=9.75 (1H, s), 7.62 (1H, d, J=3.8 Hz), 7.49 (1H, d, J=3.8 Hz), 3.88 (3H, s).
$^{13}$C NMR (100.62 MHz, CDCl$_3$): δ=52.54, 118.63, 118.75, 147.62, 153.87, 158.38, 178.92.
MS (GC-MS, 70 eV): m/z (%)=154 (55) [M$^+$], 123 (100), 109 (2), 95 (24), 67 (6), 53 (5), 39 (23).

Methyl 5-formyl-2-furoate (dimethyl acetal)

$^1$H NMR (400.17 MHz, CDCl$_3$): δ=7.16 (1H, d, J=3.5 Hz), 6.54 (1H, d, J=3.5 Hz), 5.46 (1H, s), 3.89 (3H, s), 3.37 (6H, s).
$^{13}$C NMR (100.62 MHz, CDCl$_3$): δ=51.84, 53.02, 97.52, 110.32, 118.33, 144.27, 155.03, 158.95.
MS (GC-MS, 70 eV): m/z (%)=200 (5) [M$^+$], 169 (100), 153 (4), 141 (10), 123 (20), 109 (3), 95 (3), 82 (3), 75 (10), 67 (3), 59 (7), 53 (4), 39 (8).

Example 7

Preparation of dimethyl FDCA from methyl 5-formyl-2-furoate

A 15 mL glass liner was charged with a magnetic stirring bar, methyl 5-formyl-2-furoate (117 mg, 0.76 mmol), methanol (10 mL) and sodium methoxide (4 mg, 0.076 mmol) to give a clear solution. A 1.2 wt % Au/TiO$_2$ (41.5 mg, 2.53 mmol Au) catalyst was added to give a purple suspension and the vial was placed in a 75 mL Parr Hastelloy C-276 reactor. The reactor was closed and flushed 3× with compressed air and then pressurized at 4.6 bar. Stirring was started (600 rpm) and the reaction was allowed to proceed at room temperature. After 19 h, the reaction had consumed 0.25 bar of air and the reactor was opened. The reaction mixture was filtered over Celite to remove the catalyst, which was washed with a little methanol and dichloromethane. The combined organic layers were washed with water, dried over MgSO$_4$, filtered, and the solvent was removed under reduced pressure. 2,5-FDCA dimethyl ester was obtained as light yellow crystals (106 mg, yield 76%). The product was analyzed by $^1$H/$^{13}$C-NMR and GC-MS.

Analytical Data:
$^1$H NMR (400.17 MHz, CDCl$_3$): δ=7.22 (2H, s), 3.94 (6H, s).
$^{13}$C NMR (100.62 MHz, CDCl$_3$): δ=52.33, 118.41, 153.86, 158.37.
MS (GC-MS, 70 eV): m/z (%)=184 (32) [M$^+$], 153 (100), 139 (1), 125 (6), 113 (1), 95 (8), 82 (2), 69 (6), 59 (9), 53 (4), 38 (9).

Example 8

Preparation of methyl 5-formyl-2-furoate (mixture of free aldehyde and dimethyl acetal) from 5-keto-L-galactonic acid (mono basic calcium salt)

General Procedure:
A 50 mL round bottom flask was equipped with a magnetic stirring bar, a reflux condenser with N$_2$-inlet and 5-keto-L-galactonic acid mono-basic calcium salt (1.0 g, 4 mmol). Methanol (10 mL) was added, to give a yellow suspension. Sulfuric acid (0.32 mL, 60 mmol) was added and the reaction mixture was subsequently heated to reflux (65° C.). Upon addition of the sulfuric acid, slow disappearance of the yellow color was observed, and after a few minutes the suspension turned white. After 20 h, the resulting pink suspension was allowed to cool down to room temperature and 20 mL diethyl ether was added. The resulting suspension was transferred to a separation funnel and the organic phase was washed with brine until the pH of the aqueous phase was neutral. The organic layer was dried over MgSO$_4$, filtered and concentrated at 40° C. under vacuum using a rotary evaporator. The product (167 mg, yield 22%) was obtained as red-brown oil, consisting of a mixture of methyl 5-formyl-2-furoate (free aldehyde) and methyl 5-formyl-2-furoate (dimethyl acetal).

The invention claimed is:

1. A process for the preparation of furan-2,5-dicarboxylic acid, or a carboxylic derivative thereof, comprising making 5-formyl-2-furoic acid, or a carboxylic derivative thereof, by a method comprising the steps of (i) providing an uronic acid; (ii) subjecting the uronic acid to isomerization so as to form the corresponding 5-keto-aldonic acid; (iii) subjecting said 5-keto-aldonic acid to cyclodehydration so as to produce 5-formyl-2-furoic acid or a carboxylic derivative thereof, and subjecting the 5-formyl-2-furoic acid, or the carboxylic derivative thereof, to oxidation so as to form furan-2,5-dicarboxylic acid, or a carboxylic derivative thereof.

2. A process according to claim 1, wherein the oxidation is conducted by subjecting the 5-formyl-2-furoic acid or carboxylic derivative thereof to molecular oxygen under the influence of a supported noble metal catalyst, preferably selected from the group consisting of gold, platinum, ruthenium and palladium.

3. A process according to claim 2, wherein the oxidation is conducted in the presence of a base.

4. A process according to claim 3, wherein the catalyst support is carbon.

5. A process according to claim 1, wherein the uronic acid is obtained from bio-based pectins or biobased alginates.

6. A process for the preparation of 5-formyl-2-furoic acid, or a carboxylic derivative thereof, from an uronic acid obtained from bio-based pectins or biobased alginates, the method comprising the steps of (i) providing an uronic acid obtained from bio-based pectins or biobased alginates; (ii) subjecting the uronic acid to isomerization so as to form the corresponding 5-keto-aldonic acid; (iii) subjecting said 5-keto-aldonic acid to cyclodehydration so as to produce 5-formyl-2-furoic acid or a carboxylic derivative thereof.

7. A process according to claim 6, wherein the uronic acid is selected from the group consisting of D-galacturonic acid, D-glucuronic acid, D-mannuronic acid, and mixtures thereof.

8. A process according to claim 6, wherein the 5-formyl-2-furoic acid or a carboxylic derivative thereof is C$_{1-12}$ alkyl-5-formyl-2-furoate, preferably C$_{1-4}$ alkyl-5-formyl-2-furoate.

9. A process according to claim 6, wherein the isomerization step is conducted in water in the presence of calcium hydroxide, or a calcium salt under alkaline conditions.

10. A process according to claim 6, wherein the cyclodehydration step is conducted in a solvent in the presence of an acid catalyst.

11. A process according to claim 10, wherein the acid is a Brønstedt acid, preferably selected from the group consisting of HCl, sulfuric acid, formic acid, acetic acid, oxalic acid, hydrobromic acid, phosphorous acid, and p-toluene sulfonic acid.

12. A process according to claim 10, wherein the acid is a Lewis acid selected from the group consisting of ZnCl$_2$, CuCl$_2$, BF$_3$—OEt$_2$, and lanthanide salts.

13. A bio-based process for the synthesis of furan-2,5-dicarboxylic acid, or a carboxylic derivative thereof, the process comprising the steps of (i) providing at least one bio-based uronic acid; (ii) subjecting the at least one uronic acid to isomerization so as to form the corresponding 5-keto-aldonic acid; (iii) subjecting said 5-keto-aldonic acid to cyclodehydration so as to produce 5-formyl-2-furoic acid or a carboxylic derivative thereof, subjecting the 5-formyl-2-furoic acid, or the carboxylic derivative thereof, to oxidation so as to form furan-2,5-dicarboxylic acid, or a carboxylic derivative thereof.

14. A process according to claim 10, wherein the solvent is selected from the group consisting of methanol, ethanol, water, biphasic systems, and mixtures thereof.

15. A process according to claim 14, wherein the biphasic system comprises water/methyl isobutyl ketone.

* * * * *